United States Patent [19]

Kunikata

[11] Patent Number: 5,516,934
[45] Date of Patent: May 14, 1996

[54] PROCESS FOR PRODUCING MONO-P-NITROBENZYL MALONATE

[75] Inventor: Kenji Kunikata, Ohmiya, Japan

[73] Assignee: Nippon Kayaku Kabushiki Kaisha, Tokyo, Japan

[21] Appl. No.: 495,797

[22] Filed: Jun. 27, 1995

[51] Int. Cl.⁶ .................................................. C07C 69/38
[52] U.S. Cl. .............................................. 560/193; 560/20
[58] Field of Search ........................................ 560/20, 193

[56] References Cited

U.S. PATENT DOCUMENTS 5,087,734  2/1992  Ishikura et al. .................. 560/193

FOREIGN PATENT DOCUMENTS 57-159761  3/1982  Japan .
58-208292  4/1983  Japan .
482863     9/1992  Japan .
474183    11/1992  Japan .

*Primary Examiner*—José G. Dees
*Assistant Examiner*—Samuel Barts
*Attorney, Agent, or Firm*—Nields & Lemack

[57] ABSTRACT

The present invention aims at providing a process for economically producing mono-p-nitrobenzyl malonate while recovering the excessive malonic acid and treating the by-product. The process of the present invention for producing mono-p-nitrobenzyl malonate comprises reacting p-nitrobenzyl-alcohol with malonic acid in an organic solvent, which may contain di-p-nitrobenzyl malonate if necessary, cooling the reaction mixture thus obtained to 35° to 100° C., separating the malonic acid thus precipitated and treating the reaction mixture with a basic aqueous solution at 35° to 80° C. The di-p-nitrobenzyl malonate formed as the by-product is effectively utilized by hydrolyzing or reacting with malonic acid to thereby give mono-p-nitrobenzyl malonate.

5 Claims, No Drawings

PROCESS FOR PRODUCING MONO-P-NITROBENZYL MALONATE

This invention relates to a process for producing a pharmaceutical intermediate. More particularly, it relates to a process for producing mono-p-nitrobenzyl malonate.

Mono-p-nitrobenzyl malonate is an important intermediate in the production of medicines.

There have been reported in literature few processes for producing mono-p-nitrobenzyl malonate industrially. For example, Japanese Patent Laid-Open No. 159761/1982 has disclosed a process therefor which comprises reacting Meldrum's acid with p-nitrobenzyl alcohol in acetonitrile, while Japanese Patent Laid-Open No. 208292/1983 has disclosed another process therefor which comprises reacting malonic acid with p-nitrobenzyl chloride in dimethylformamide. However these processes are disadvantageous from an industrial viewpoint because of the expensive starting materials, a low yield, etc.

As described above, the conventional processes for producing mono-p-nitrobenzyl malonate either require a complicated procedure or fail to industrially produce mono-p-nitrobenzyl malonate at a low cost. Therefore it has been required to develop a process for economically producing mono-p-nitrobenzyl malonate.

The present inventors have concentrated their energy on a process which comprises reacting malonic acid with p-nitrobenzyl alcohol in the presence of an organic solvent to thereby form mono-p-nitrobenzyl malonate while removing the thus formed water from the reaction system through azeotropic distillation, thus completing the present invention. When a solvent such as benzene, toluene, xylene or chlorobenzene is used in the reaction, malonic acid is hardly soluble in the solvent. Therefore an increase in the amount of malonic acid (relative to p-nitrobenzyl alcohol), which aims at reducing the amount of the di-p-nitrobenzyl malonate formed in the reaction, scarcely contributes to the reduction of the amount of the di-p-nitrobenzyl malonate thus formed, since the malonic acid is precipitated as crystals and thus separated out from the reaction system. When the reaction mixture is completely cooled, malonic acid, mono-p-nitrobenzyl malonate and di-p-nitrobenzyl malonate are precipitated together and thus malonic acid cannot be separated from the mixture, which increases the waste water load and thus results in an economical disadvantage. Although it is known that the formation of di-p-nitrobenzyl malonate can be suppressed by using malonic acid at a larger ratio to p-nitrobenzyl alcohol, it is impossible to recover malonic acid and thus the ratio of malonic acid cannot be elevated.

In the production of mono-p-nitrobenzyl malonate by reacting malonic acid with p-nitrobenzyl alcohol, conditions for separating the mono-p-nitrobenzyl malonate are discussed in detail. As a result, it has been found out that when the reaction mixture, which is a heterogenous liquid-liquid mixture, is carefully cooled after the completion of the reaction, malonic acid is precipitated at 35° to 100° C. while mono-p-nitrobenzyl malonate and di-p-nitrobenzyl malonate are obtained in the state of being dissolved in the reaction solvent and thus the excessive malonic acid can be efficiently recovered, though these phenomena somewhat vary depending on the type and amount of the reaction solvent and the ratio of the feedstocks. Then mono-p-nitrobenzyl malonate is extracted from the reaction mixture, from which malonic acid has been removed, with a basic aqueous solution at 35° to 80° C. and acid-precipitated. Thus crystals having a high purity and showing a high filtration rate can be obtained.

It has been also revealed that when malonic acid is reacted with p-nitrobenzyl alcohol to thereby form mono-p-nitrobenzyl malonate, the formation of di-p-nitrobenzyl malonate can be suppressed by preliminarily adding di-p-nitrobenzyl malonate to the reaction mixture.

The reaction between malonic acid and p-nitrobenzyl alcohol is always accompanied by the formation of di-p-nitrobenzyl malonate as a by-product. Unless a method for economically treating di-p-nitrobenzyl malonate is established, therefore, little industrial merit can be achieved by reacting malonic acid with p-nitrobenzyl alcohol.

The present inventors have conducted extensive studies on the treatment of the di-p-nitrobenzyl malonate formed as a by-product. As a result, they have found out it is highly effective in the industrial production of mono-p-nitrobenzyl malonate that the di-p-nitrobenzyl malonate is converted into p-nitrobenzyl alcohol through hydrolysis or and then recycled using the resulting alcohol as the starting material or the di-p-nitrobenzyl malonate formed as the by-product is reacted with malonic acid to thereby give mono-p-nitrobenzyl malonate. The present invention has been thus completed.

Accordingly, the present invention relates to:

(1) A process for producing mono-p-nitrobenzyl malonate which comprises reacting p-nitrobenzyl alcohol with malonic acid in an organic solvent, cooling the reaction mixture thus obtained to 35° to 100° C., separating the malonic acid thus precipitated, treating the reaction mixture with a basic aqueous solution at 35° to 80° C. and then extracting mono-p-nitrobenzyl malonate therefrom.

(2) A process for producing mono-p-nitrobenzyl malonate which comprises reacting p-nitrobenzyl alcohol with malonic acid in an organic solvent containing di-p-nitrobenzyl malonate, cooling the reaction mixture thus obtained to 35° to 100° C., separating the malonic acid thus precipitated, treating the reaction mixture with a basic aqueous solution at 35° to 80° C. and then extracting mono-p-nitrobenzyl malonate therefrom.

(3) A process for producing mono-p-nitrobenzyl malonate as described in the above (1) or (2) wherein said organic solvent is one selected from the group consisting of toluene, xylene, monochlorobenzene and dichlorobenzene.

(4) A process for producing mono-p-nitrobenzyl malonate as described in the above (1) or (2) wherein di-p-nitrobenzyl malonate, which is contained in the reaction mixture after the extraction of mono-p-nitrobenzyl malonate in the process for producing mono-p-nitrobenzyl malonate as described in the above (1) or (2), is hydrolyzed to thereby give p-nitrobenzyl alcohol which is then used as the starting material.

(5) A process for producing mono-p-nitrobenzyl malonate as described in the above (1) or (2) wherein di-p-nitrobenzyl malonate, which is contained in the reaction mixture after the extraction of mono-p-nitrobenzyl malonate in the process for producing mono-p-nitrobenzyl malonate as described in the above (1) or (2), is converted into mono-p-nitrobenzyl malonate by reacting with malonic acid.

Now, the present invention will be described in detail.

[1] Step of producing mono-p-nitrobenzyl malonate by reacting p-nitrobenzyl alcohol with malonic acid:

The molar ratio of malonic acid/p-nitrobenzyl alcohol is usually from 1.0 to 10.0, preferably from 1.2 to 5.0 and still preferably from 1.5 to 3.0. A molar ratio exceeding 10.0 causes a decrease in the volume efficiency of the reaction vessel. On the other hand, a molar ratio less than 1.0 results in the formation of a large amount of di-p-nitrobenzyl malonate and thus lowers the yield.

The reaction temperature is usually from 30° to 150° C., preferably from 40° to 130° C., still preferably from 60° to 120° C. and particularly preferably from 70° to 115° C. A reaction temperature exceeding 150° C. causes the decomposition of malonic acid and thus lowers the yield. In this case, there arises another problem of the formation of p-nitrobenzyl acetate, i.e., an impurity. On the other hand, a reaction temperature lower than 30° C. is economically disadvantageous because of the low reaction rate.

The reaction time ranges from 0.2 to 10 hours, preferably from 0.5 to 6 ours and still preferably from 1.0 to 3 hours.

Examples of the organic solvent usable in the reaction include aromatic compounds such as benzene, toluene, xylene, ethylbenzene, cumene, mesitylene, durene, tetralin, butylbenzene, p-cymene, chylohexylbenzene, diethylbenzene, pentylbenzene, dipentylbenzene, dodecylbenzene, chlorobenzene and o-dichlorobenzene; alicyclic compounds such as cyclopentane, methylcyclopentane, cyclohexane, methylcyclohexane, ethylcyclohexane, p-menthane, bicyclohexyl and decalin; aliphatic compounds such as hexane, 2-methylpentane, 2,2-dimethylbutane, 2,3-dimethylbutane, heptane, octane, 2,2,3-trimethylpentane, isooctane, nonane, 2,2,5-trimethylhexane, decane and dodecane; halogenated hydrocarbons such as dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane and hexachloroethane; and ethers such as dipropyl ether, diisopropyl ether, dibutyl ether and dihexyl ether. Among these organic solvents, benzene, toluene, xylene, chlorobenzene and dichlorobenzene are preferable and toluene and dichlorobenzene are particularly preferable therefor. The above solvent may be used by mixing with one or more solvents one another.

The organic solvent is used usually in an amount of from 100 to 5,000% by weight, preferably from 200 to 3,000% by weight and still preferably from 300 to 2,000% by weight, each based on malonic acid. It is also possible to add a small amount (for example, 0 to 3% by weight based on the organic solvent) of water thereto.

Although the reaction proceeds without using any catalyst, it is effective to use a catalyst, for example, p-toluenesulfonic acid monohydrate, sulfuric acid or hydrochloric acid. p-Toluenesulfonic acid monohydrate may be cited as a particularly preferable catalyst.

It is preferable that the water formed in the reaction is removed from the reaction system by azeotropic distillation under atmospheric or reduced pressure. As the reaction proceeds, the mono-p-nitrobenzyl malonate thus formed is gradually converted into di-p-nitrobenzyl malonate and, therefore, the yield of mono-p-nitrobenzyl malonate once attaining a peak is slowly decreased. Accordingly, it is preferable to cease the reaction in the course of the same. However it is difficult to separate the target mono-p-nitrobenzyl malonate from the feedstock p-nitrobenzyl alcohol, since they are similar to each other in polarity. Thus it is necessary to react the p-nitrobenzyl alcohol within an acceptable range. That is to say, the reaction product is sampled during the reaction and analyzed by liquid chromatography (HPLC) and the reaction is ceased when the ratio of p-nitrobenzyl alcohol is from 0.05 to 50.0% by area in usual, preferably from 0.1 to 30.0% by area, still preferably from 0.2 to 10.0% by area and particularly preferably from 0.3 to 1.0% by area.

Alternatively, the reaction between p-nitrobenzyl alcohol and malonic acid may be effected in the following manner.

Namely, p-nitrobenzyl alcohol, malonic acid and a catalyst are added to an organic solvent, which is hardly soluble in water, containing di-p-nitrobenzyl malonate. Then the reaction is carried out in the same manner as the one described above. The p-nitrobenzyl alcohol is used in an amount of usually from 10 to 1,000% by weight, preferably from 100 to 600% by weight and still preferably from 200 to 400% by weight, each based on the di-p-nitrobenzyl malonate.

In this reaction, such an organic solvent as those described above is used in an amount of usually from 100 to 5,000% by weight, preferably from 200 to 3,000% by weight and still preferably from 300 to 1,000% by weight, each based on the sum of the di-p-nitrobenzyl malonate and p-nitrobenzyl alcohol. It is also possible to add a small amount (for example, from 0 to 3% by weight based on the organic solvent) of water thereto.

Subsequently, the reaction mixture is treated in the same manner as the one described above.

By preliminarily adding di-p-nitrobenzyl malonate to the organic solvent to be used in the reaction, the formation of di-p-nitrobenzyl malonate as a by-product can be suppressed.

[2]Step of taking out mono-p-nitrobenzyl malonate and recovering malonic acid:

After the completion of the reaction of [1], the reaction mixture is carefully cooled usually to from 35° to 100° C., preferably from 40° to 80° C., still preferably from 45° to 70° C. and particularly preferably from 50° to 60° C. Thus malonic acid is precipitated alone. Then the malonic acid is separated from the reaction mixture by sucking up the supernatant liquid or filtering the reaction mixture. After removing the malonic acid, the reaction mixture is maintained usually at from 35° to 80° C., preferably from 40° to 60° C. and still preferably from 40° to 50° C. After adding water, a basic substance is added thereto in small portions and the alkali salt of mono-p-nitrobenzyl malonate is extracted from the reaction solvent into the aqueous system. Water is added in an amount of usually from 300 to 2,000% by weight, preferably from 400 to 1,500% by weight and still preferably from 500 to 1,300% by weight, each based on the mono-p-nitrobenzyl malonate thus formed.

The basic substance usable herein is exemplified by sodium carbonate, potassium carbonate, sodium hydrogencarbonate, potassium hydrogencarbonate, sodium hydroxide and potassium hydroxide. Among these substances, potassium carbonate and potassium hydrogencarbonate are particularly preferable therefor from the viewpoint of solubility.

The alkali salt of mono-p-nitrobenzyl malonate is easily hydrolyzed in water. When the pH value of the extracting aqueous solution is elevated, in particular, it is quickly hydrolyzed at room temperature. Therefore, the pH value is regulated usually not more than 7.5, preferably not more than 7.0, still preferably not more than 6.5 and particularly preferably not more than 5.8 by adding the basic substance thereto in small portions.

The extraction is effected usually for from 0.1 to 2.0 hours, preferably from 0.2 to 1.5 hours, still preferably from 0.3 to 1.0 hour and particularly preferably from 0.5 to 0.7 hours. The aqueous solution of the alkali salt of mono-p-nitrobenzyl malonate thus extracted may be washed with an organic solvent hardly soluble in water (for example, benzene, toluene, cyclohexane, etc.).

The mono-p-nitrobenzyl malonate may be acid-precipitated from the alkali salt thereof by adjusting the pH value to 3.0 by adding an aqueous solution of sulfuric acid or hydrochloric acid in small portions, stirring the mixture as such, filtering it under reduced pressure, washing the filtration cake with a small amount of water and then drying it at

[3] Method for treating di-p-nitrobenzyl malonate:

The reaction between malonic acid and p-nitrobenzyl alcohol is always accompanied by the formation of di-p-nitrobenzyl malonate as a by-product. In the process for producing mono-p-nitrobenzyl malonate by reacting malonic acid with p-nitrobenzyl alcohol, it is highly important to effectively utilize this di-p-nitrobenzyl malonate.

The di-p-nitrobenzyl malonate formed as the by-product can be effectively utilized by the following two methods.

(1) Method for producing p-nitrobenzyl alcohol by hydrolyzing di-p-nitrobenzyl malonate:

After extracting mono-p-nitrobenzyl malonate, preferably in the form of its potassium salt in [2], di-p-nitrobenzyl malonate is obtained in a state of being dissolved in the organic solvent. Thus the di-p-nitrobenzyl malonate can be isolated by cooling the reaction mixture and filtering off the di-p-nitrobenzyl malonate thus precipitated or distilling off the organic solvent.

The di-p-nitrobenzyl malonate can be hydrolyzed either in the isolated form or in the state of being dissolved in the organic solvent. It is usually reasonable not to isolate the di-p-nitrobenzyl malonate.

The reaction temperature is usually from $-^\circ$ to $100^\circ$ C., preferably from $0^\circ$ to $60^\circ$ C. and still preferably from $10^\circ$ to $40^\circ$ C. When the reaction temperature is lower than $-^\circ$ C., the solubilities of the starting materials are low and the reaction proceeds at a low rate. When the reaction temperature exceeds $100^\circ$ C., on the other hand, the by-product is formed in a large amount.

The basic substance to be used in the hydrolysis is exemplified by sodium carbonate, potassium carbonate, sodium hydrogencarbonate, potassium hydrogencarbonate, sodium hydroxide and potassium hydroxide. Among these substances, sodium hydroxide and potassium hydroxide are particularly preferable. Such a basic substance is used in an amount of usually from 0.05 to 10 mol, preferably from 0.1 to 3.0 mol and still preferably from 0.3 to 1.0 mol, each per mol of the di-p-nitrobenzyl malonate.

Water is used in an amount of usually from 10 to 1,000% by weight, preferably from 20 to 300% by weight and still preferably from 30 to 200% by weight, each based on the di-p-nitrobenzyl malonate.

In order to elevate the mutual solubility between the di-p-nitrobenzyl malonate and the basic aqueous solution, a lower alcohol such as methanol, ethanol or isopropanol may be added and thus the reaction rate can be extremely elevated. Such an alcohol may be used in an amount of usually from 5 to 5,000% by weight, preferably from 20 to 2,000% by weight, still preferably from 30 to 1,000% by weight and particularly preferably from 35 to 200% by weight, each based on the di-p-nitrobenzyl malonate.

The di-p-nitrobenzyl malonate, which is obtained by removing the malonic acid and the mono-p-nitrobenzyl malonate from the reaction mixture as described in [2], is usually contained in an organic solvent hardly soluble in water such as benzene, toluene, xylene or chlorobenzene. The content of the di-p-nitrobenzyl malonate may be controlled by removing or adding the organic solvent. The organic solvent hardly soluble in water is used usually in an amount of from 0 to 5,000% by weight, preferably from 0 to 1,000% by weight, each based on the di-p-nitrobenzyl malonate.

After the completion of the hydrolysis, the reaction mixture is neutralized by adding an inorganic acid (for example, hydrochloric acid, sulfuric acid, etc.) in the equivalent amount to the basic substance employed. Next, the reaction mixture is heated and the lower alcohol is distilled off, if necessary. Thus a layer of the organic solvent hardly soluble in water, which contains the p-nitrobenzyl alcohol, and an aqueous layer which contains the malonic acid, the salt, etc., are obtained. After separating the aqueous layer, the organic solvent layer is optionally washed with water. Then it is usable as the starting material in [1]. Although it is possible to obtain the p-nitrobenzyl alcohol by distilling off the organic solvent, it is reasonable to subject the organic solvent layer to the reaction without distillation. It is also possible not to separate the aqueous layer but use the reaction mixture as the starting material in [1]. In such a case, however, it is recommended to minimize the amount of water and the basic substance used in the hydrolysis.

This method for producing p-nitrobenzyl alcohol by hydrolyzing di-p-nitrobenzyl malonate is a novel one.

(2) Method for obtaining mono-p-nitrobenzyl malonate by reacting di-p-nitrobenzyl malonate with malonic acid:

The di-p-nitrobenzyl malonate to be used herein may be either an isolated substance or one obtained in [2] in the form of being dissolved in the organic solvent hardly soluble in water. The molar ratio of malonic acid/di-p-nitrobenzyl malonate ranges usually from 1.0 to 10.0, preferably from 1.2 to 5.0 and still preferably from 1.5 to 3.0. When this ratio exceeds 10.0, the volume efficiency of the reaction vessel is lowered. When it is less than 1.0, on the other hand, the conversion ratio is lowered and thus only a poor yield is achieved.

The reaction temperature is usually from $30^\circ$ to $150^\circ$ C., preferably from $40^\circ$ to $130^\circ$ C., still preferably from $60^\circ$ to $120^\circ$ C. and particularly preferably from $70^\circ$ to $115^\circ$ C. A reaction temperature exceeding $150^\circ$ C. causes the decomposition of malonic acid and thus lowers the yield. In this case, there arises another problem of the formation of p-nitrobenzyl acetate, i.e., an impurity. On the other hand, a reaction temperature lower than $30^\circ$ C. is economically disadvantageous because of the low reaction rate.

The reaction is effected usually for from 0.2 to 10 hours, preferably from 0.5 to 6 hours and still preferably from 1.0 to 3 hours.

Examples of the organic solvent usable in the reaction include nitro compounds such as o-nitrotoluene, m-nitrotoluene, p-nitrotoluene and nitrobenzene; aromatic compounds such as benzene, toluene, xylene, ethylbenzene, cumene, mesitylene, durene, tetralin, butylbenzene, p-cymene, chylohexylbenzene, diethylbenzene, pentylbenzene, dipentylbenzene, dodecylbenzene, chlorobenzene and o-dichlorobenzene; alicyclic compounds such as cyclopentane, methylcyclopentane, cyclohexane, methylcyclohexane, ethylcyclohexane, p-menthane, bicyclohexyl and decalin; aliphatic compounds such as hexane, 2-methylpentane, 2,2-dimethylbutane, 2,3-dimethylbutane, heptane, octane, 2,2,3-trimethylpentane, isooctane, nonane, 2,2,5-trimethylhexane, decane and dodecane; halogenated hydrocarbons such as dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane and hexachloroethane; and ethers such as dipropyl ether, diisopropyl ether, dibutyl ether and dihexyl ether.

The organic solvent is used in an amount of usually from 100 to 5,000% by weight, preferably from 200 to 3,000% by weight and still preferably from 300 to 2,000% by weight, each based on the malonic acid.

As a catalyst, use can be effectively made of p-toluenesulfonic acid monohydrate, methanesulfonic acid, sulfuric acid or hydrochloric acid. p-Toluenesulfonic acid monohydrate may be cited as a particularly preferable catalyst.

Next, the procedure described in the above [1] is repeated to thereby give mono-p-nitrobenzyl malonate. The method whereby mono-p-nitrobenzyl malonate is obtained from di-p-nitrobenzyl malonate is a novel one.

According to the process of the present invention, the excessive malonic acid can be efficiently separated from the reaction mixture, which relieves the waste water load. In this process, further, the di-p-nitrobenzyl malonate formed as the by-product is efficiently utilized. Accordingly, it is a highly efficient process for producing mono-p-nitrobenzyl malonate from p-nitrobenzyl alcohol and malonic acid. Moreover, the process of the present invention is characterized in that mono-p-nitrobenzyl malonate having a high purity can be obtained at a high overall yield thereby.

To further illustrate the present invention in greater detail, and not by way of limitation, the following examples will be given. In these examples, every % is by weight.

EXAMPLE 1

To a four-necked flask (200 cc) provided with a stirrer, a thermometer and a water separator were added 15.3 g of p-nitrobenzyl alcohol, 15.6 g of malonic acid, 0.25 g of p-toluenesulfonic acid monohydrate and 100 cc of toluene at room temperature. The mixture was then heated to 110° C. over 2 hours. During the following 1 hour, the toluene was refluxed at 110° to 112° C. while removing water from the reaction system through azeotropic distillation. Then the reaction mixture was cooled to 50° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 15 cc of toluene and the wash liquid was transferred into the above-mentioned 300 cc flask (malonic acid recovered: 5.2 g.

150 cc of water was further introduced into this 300 cc flask and maintained at 40° C. Thus crystals were precipitated. Electrodes for measuring pH value were inserted thereinto and the mixture was thoroughly stirred. Then potassium carbonate was added thereto over about 15 minutes until the pH value reached 5.4. Thus 5.7 g of potassium carbonate was used. After allowing to stand, the aqueous layer (i.e., the lower layer) thus separated out was taken up and washed with about 50 cc of toluene. Then a 20% aqueous solution of sulfuric acid was slowly added thereto to thereby adjust the pH value to 3.0. Thus 17 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 15.5 g (65%, based on p-nitrobenzyl alcohol). m.p.: 107° to 110° C. Purity determined by liquid chromatography: 99.8% by area.

EXAMPLE 2

To a four-necked flask (200 cc) provided with a stirrer, a thermometer and a water separator were added 15.3 g of p-nitrobenzyl alcohol, 20.8 g of malonic acid, 0.25 g of p-toluenesulfonic acid monohydrate and 100 cc of toluene at room temperature. The mixture was then heated to 110° C. over 2 hours. During the following 1 hour, the toluene was refluxed at 110° to 112° C. while removing water from the reaction system through azeotropic distillation. Then the reaction mixture was cooled to 50° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 25 cc of toluene and the wash liquid was transferred into the above-mentioned 300 cc flask (malonic acid recovered: 9.6 g).

150 cc of water was further introduced into this 300 cc flask and maintained at 40° C. Thus crystals were precipitated. Electrodes for measuring pH value were inserted thereinto and the mixture was thoroughly stirred. Then potassium carbonate was added thereto over about 15 minutes until the pH value reached 5.8. Thus 6.0 g of potassium carbonate was used. After allowing to stand, the aqueous layer (i.e., the lower layer) thus separated out was taken up and washed with about 50 cc of toluene. Then a 20% aqueous solution of sulfuric acid was slowly added thereto to thereby adjust the pH value to 3.0. Thus 19 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 17.2 g (72%, based on p-nitrobenzyl alcohol). m.p.: 107° to 110° C. Purity determined by liquid chromatography: 99.7% by area.

EXAMPLE 3

To a four-necked flask (200 cc) provided with a stirrer and a thermometer were added 6.4 g of di-p-nitrobenzyl malonate, 64 cc of toluene and 27 cc of methanol at room temperature and thus the di-p-nitrobenzyl malonate was dissolved. Further 7 g of water was added thereto and thus the reaction mixture became cloudy. The reaction mixture was cooled to 10° C. and 2.7 g of a 28% aqueous solution of sodium hydroxide was dropped thereinto over 30 minutes. Next, the reaction mixture was maintained at 10° to 20° C. for 1 hour and thus the hydrolysis was completed. Then the pH value of the reaction mixture was adjusted to 5 to 6 with a 20% aqueous solution of sulfuric acid followed by heating. The distillation of methanol began at the temperature of the reaction mixture of 70° C. When the amount of the mono-p-nitrobenzyl malonate distilled decreased at the temperature of the reaction mixture of 80° C., the reaction mixture was cooled and maintained at 40° C. Then the stirring was ceased and the reaction mixture was allowed to stand. The aqueous layer (i.e., the lower layer) was separated and the toluene layer was washed with 10 cc of water. The p-nitrobenzyl alcohol contained in the toluene layer was determined by liquid chromatography with the use of the p-nitrochlorobenzene as the internal standard. Yield of p-nitrobenzyl alcohol: 5.1 g. (98%, based on di-p-nitrobenzyl malonate). Purity determined by liquid chromatography: 99.8% by area.

EXAMPLE 4

To a four-necked flask (50 cc) provided with a stirrer and a thermometer were added 6.4 g of di-p-nitrobenzyl malonate, 20 cc of toluene and 2.3 g of methanol at room temperature. Then the mixture was cooled to 10° C. and 1.4 g of a 28% aqueous solution of sodium hydroxide was dropped thereinto over 10 minutes. Next, the reaction mixture was maintained at 10° to 20° C. for 1 hour. and thus the hydrolysis was completed. Then the pH value of the reaction mixture was adjusted to 5 to 6 with a 20% aqueous solution of sulfuric acid followed by heating. The distillation of methanol began at the temperature of the reaction mixture of 70° C. When the amount of the mono-p-nitrobenzyl malonate distilled decreased at the temperature of the reaction mixture of 80° C., the reaction mixture was cooled and maintained at 40° C. Then the stirring was ceased and the reaction mixture was allowed to stand. The p-nitrobenzyl alcohol contained in the toluene layer was determined by liquid chromatography with the use of the p-nitrochlorobenzene as the internal standard.

Yield of p-nitrobenzyl alcohol: 4.9 g (95%, based on di-p-nitrobenzyl malonate). Purity determined by liquid chromatography: 99.3% by area.

EXAMPLE 5

To a four-necked flask (200 cc) provided with a stirrer, a thermometer and a water separator were added 10.8 g of p-nitrobenzyl alcohol, 20.8 g of malonic acid, 5.5 g of di-p-nitrobenzyl malonate, 0.25 g of p-toluenesulfonic acid monohydrate and 100 cc of toluene at room temperature. The mixture was then heated to 110° C. over 2 hours. During the following 1 hour, the toluene was refluxed at 110° to 112° C. while removing water from the reaction system through azeotropic distillation. Then the reaction mixture was cooled to 50° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 25 cc of toluene and the wash liquid was transferred into the above-mentioned 300 cc flask (malonic acid recovered: 9.6 g).

150 cc of water was further introduced into this 300 cc flask and maintained at 40° C. Thus crystals were precipitated. Electrodes for measuring pH value were inserted thereinto and the mixture was thoroughly stirred. Then potassium carbonate was added thereto over about 15 minutes until the pH value reached 5.8. Thus 5.7 g of potassium carbonate was used. After allowing to stand, the aqueous layer (i.e., the lower layer) thus separated out was taken up and washed with about 50 cc of toluene. Then a 20% aqueous solution of sulfuric acid was slowly added thereto to thereby adjust the pH value to 3.0. Thus 17 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzylmalonate: 14.8 (62%, based on p-nitrobenzyl alcohol). m.p.: 107° to 110° C. Purity determined by liquid chromatography: 99.7% by area.

EXAMPLE 6

To a four-necked flask (200 cc) provided with a stirrer, a thermometer and a water separator were added 20.8 g of malonic acid, 5.5 g of di-p-nitrobenzyl malonate, 1.0 g of p-toluenesulfonic acid monohydrate and 100 cc of nitrobenzene at room temperature. The mixture was then heated to 107° C. over 2 hours and then allowed to react at 107° to 110° C. for 6 hours. Then the reaction mixture was cooled to 20° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 25 cc of nitrobenzene and the wash liquid was transferred into the above-mentioned 300 cc flask (malonic acid recovered: 9.6 g).

The nitrobenzene solution was analyzed by liquid chromatography with the use of p-nitrochlorobenzene as the internal standard. As a result, it was found out that 5.6 g of mono-p-nitrobenzyl malonate was obtained (yield: 80%).

EXAMPLE 7

To a four-necked flask (200 cc) provided with a stirrer, a thermometer and a water separator were added 10.4 g of p-nitrobenzyl alcohol, 4.9 g of the p-nitrobenzyl alcohol (contained in 20 cc of toluene) recovered in the above Example 4, 15.6 g of malonic acid, 0.25 g of p-toluenesulfonic acid monohydrate and 80 cc of toluene at room temperature. The mixture was then heated to 110° C. over 2 hours. During the following 1 hour, the toluene was refluxed at 110° to 112° C. while removing water from the reaction system through azeotropic distillation. Then the reaction mixture was cooled to 50° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 15 cc of toluene and the wash liquid was transferred into the above-mentioned 300 cc flask (malonic acid recovered: 5.2 g).

150 cc of water was further introduced into this 300 cc flask and maintained at 40° C. Thus crystals of mono-p-nitrobenzyl malonate were precipitated. Electrodes for measuring pH value were inserted thereinto and the mixture was thoroughly stirred. Then potassium carbonate was added thereto over about 15 minutes until the pH value reached 5.4. Thus 5.7 g of potassium carbonate was used. After allowing to stand, the aqueous layer (i.e., the lower layer) thus separated out was taken up and washed with about 50 cc of toluene. Then a 20% aqueous solution of sulfuric acid was slowly added thereto to thereby adjust the pH value to 3.0. Thus 17 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 15.5 g (65%, based on p-nitrobenzyl alcohol). m.p.: 107° to 110° C. Purity determined by liquid chromatography: 99.8% by area.

EXAMPLE 8

To a four-necked flask (200 cc) provided with a stirrer, and a thermometer were added the solution of di-p-nitrobenzyl malonate in toluene (di-p-nitrobenzyl malonate: 6.2 g, toluene: 100 cc) obtained in the above Example 1 and 27 cc of methanol at room temperature and thus the di-p-nitrobenzyl malonate was dissolved. Further 7 g of water was added thereto and thus the reaction mixture became cloudy. The reaction mixture was cooled to 10° C. and 2.7 g of a 28% aqueous solution of sodium hydroxide was dropped thereinto over 30 minutes. Next, the reaction mixture was maintained at 10° to 20° C. for 1 hour and thus the hydrolysis was completed. Then the pH value of the reaction mixture was adjusted to 5 to 6 with a 20% aqueous solution of sulfuric acid followed by heating. The distillation of methanol began at the temperature of the reaction mixture of 70° C. When the amount of the methanol distilled decreased at the temperature of the reaction mixture of 80° C., the reaction mixture was cooled and maintained at 40° C. Then the stirring was ceased and the reaction mixture was allowed to stand. The aqueous layer (i.e., the lower layer) was separated and the toluene layer was washed with 10 cc of water. The p-nitrobenzyl alcohol contained in the toluene layer was determined by liquid chromatography with the use of the p-nitrochlorobenzene as the internal standard.

Yield of p-nitrobenzyl alcohol: 5.0 g (98%, based on di-p-nitrobenzyl malonate). Purity determined by liquid chromatography: 99.8% by area.

EXAMPLE 9

To a four-necked flask (200 cc) provided with a stirrer, a thermometer and a water separator were added 10.8 g of p-nitrobenzyl alcohol, 20.8 g of malonic acid, the solution of di-p-nitrobenzyl malonate in toluene (di-p-nitrobenzyl malonate: 5.0 toluene: 100 cc) obtained in the above Example 2 and 0.25 g of p-toluenesulfonic acid monohydrate at room temperature. The mixture was then heated to 110° C. over 2 hours. During the following 1 hour, the toluene was refluxed at 110° to 112° C. while removing water from the reaction system through azeotropic distillation. Then the reaction mixture was cooled to 50° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 25 cc of toluene and the washing liquor was transferred into the above-mentioned 300 cc flask (malonic acid recovered: 9.6

150 cc of water was further introduced into this 300 cc flask and maintained at 40° C. Thus crystals were precipitated. Electrodes for measuring pH value were inserted thereinto and the mixture was thoroughly stirred. Then potassium carbonate was added thereto over about 15 minutes until the pH value reached 5.8. Thus 5.7 g of potassium carbonate was used. After allowing to stand, the aqueous layer (i.e., the lower layer) thus separated out was taken up and washed with about 50 cc of toluene. Then a 20% aqueous solution of sulfuric acid was slowly added thereto to thereby adjust the pH value to 3.0. Thus 17 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 14.8 g (62%, based on p-nitrobenzyl alcohol). m.p.: 107° to 110° C. Purity determined by liquid chromatography: 99.7% by area.

EXAMPLE 10

To a four-necked flask (300 cc) provided with a stirrer, a thermometer and a water separator were added 15.3 g of p-nitrobenzyl alcohol, 31.2 g of malonic acid, 0,125 g of p-toluenesulfonic acid monohydrate and 30 cc of o-dichlorobenzene at room temperature. The mixture was then heated and 1 g of water was added thereto at 70° C. The mixture was heated to 100° C. over 1 hour and maintained at 100° C. for the following 30 minutes. Then the pressure in the reaction system was reduced to 170 mmHg and thus water and the o-dichlorobenzene underwent azeotropic distillation, while dropping o-dichlorobenzene thereinto in small portions. After 1.5 hours, the reaction temperature had been elevated to 110° C. and, during this period, 7 cc of o-dichlorobenzene and 2 cc of water had been distilled off and 5 cc of o-dichlorobenzene had been dropped. The pressure in the reaction system was 125 mmHg. Next, the pressure in the reaction system was returned to the atmospheric level and 75 cc of o-dichlorobenzene was added. The reaction mixture was cooled to 40° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 30 cc of hot o-dichlorobenzene and the wash liquid was transferred into the above-mentioned 300 cc flask (malonic acid recovered: 18.2 g).

50 cc of water was further introduced into this 300 cc flask and maintained at 40° C. Thus crystals were precipitated. Electrodes for measuring pH value were inserted thereinto and the mixture was thoroughly stirred. Then a 30% aqueous solution of potassium carbonate was added thereto over about 15 minutes until the pH value reached 5.5. Thus 23 cc of the aqueous solution was required. After allowing to stand, the aqueous layer thus separated out was taken up and washed with about 15 cc of o-dichlorobenzene. Then a 20% aqueous solution of sulfuric acid was slowly added thereto to thereby adjust the pH value to 2.5. Thus 22 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 17.9 g (74.8%, based on p-nitrobenzyl alcohol). m.p.: 107° to 110° C. Purity determined by liquid chromatography: 99.8% by area.

EXAMPLE 11

To a four-necked flask (300 cc) provided with a stirrer, a thermometer and a water separator were added 15.3 g of p-nitrobenzyl alcohol, 31.2 g of malonic acid and 36 cc of toluene at room temperature. The mixture was then heated and 1 g of water and 0.125 g of p-toluenesulfonic acid monohydrate were added thereto at 70° C. The mixture was heated to 105° C. over 1 hour and the toluene was refluxed. The reaction mixture was heated to 111° C. over about 2 hours while separating the water thus distilled. Then no water was distilled any more and the reaction had been completed. After adding 75 cc of toluene, the reaction mixture was cooled to 70° C. to thereby precipitate malonic acid. After stirring for 30 minutes and allowing to stand for 30 minutes at the same temperature, the supernatant of the reaction mixture was transferred into a 300 cc flask. Then the reaction flask and the malonic acid were washed with 30 cc of hot toluene and the wash liquid was transferred into the above-mentioned 300 cc flask (malonic acid recovered: 18.2

50 cc of water was further introduced into this 300 cc flask and maintained at 40° C. Thus crystals were precipitated. Electrodes for measuring pH value were inserted thereinto and the mixture was thoroughly stirred. Then a 30% aqueous solution of potassium carbonate was added thereto over about 15 minutes until the pH value reached 5.5. Thus 23 cc of the aqueous solution was required. After allowing to stand, the aqueous layer (i.e., the lower layer) thus separated out was taken up and washed with about 15 cc of toluene. Then a 20% aqueous solution of sulfuric acid was slowly added thereto to thereby adjust the pH value to 2.5. Thus 22 cc of the aqueous solution was used. After stirring for about 1 hour, the reaction mixture was filtered under reduced pressure. The filter cake was washed with a small amount of water and dried at 50° to 60° C. under reduced pressure.

Yield of mono-p-nitrobenzyl malonate: 17.9 g (74.8%, based on p-nitrobenzyl alcohol). m.p.: 107° to 110° C. Purity determined by liquid chromatography: 99.8% by area.

As described above, the present invention makes it possible to separate the excessive malonic acid from the reaction mixture. Thus the waste water load can be reduced and di-p-nitrobenzyl malonate formed as a by-product can be efficiently treated, which brings about economical advantages.

What we claim is:

1. A process for producing mono-p-nitrobenzyl malonate which comprises reacting p-nitrobenzyl alcohol with malonic acid in an organic solvent, cooling the reaction mixture thus obtained to 35° to 100° C., separating the malonic acid thus precipitated, treating the reaction mixture with a basic aqueous solution at 35° to 80° C. and then extracting mono-p-nitrobenzyl malonate therefrom.

2. A process for producing mono-p-nitrobenzyl malonate which comprises reacting p-nitrobenzyl alcohol with malonic acid in an organic solvent containing di-p-nitrobenzyl malonate, cooling the reaction mixture thus obtained to 35° to 100° C., separating the malonic acid thus precipitated, treating the reaction mixture with a basic aqueous solution at 35° to 80° C. and then extracting mono-p-nitrobenzyl malonate therefrom.

3. A process for producing mono-p-nitrobenzyl malonate as set forth in claim 1 or 2 wherein said organic solvent is one selected from the group consisting of toluene, xylene, monochlorobenzene and dichlorobenzene.

4. A process for producing mono-p-nitrobenzyl malonate as set forth in claim 1 or 2 wherein di-p-nitrobenzyl malonate, which is contained in the reaction mixture after the extraction of mono-p-nitrobenzyl malonate in the process for producing mono-p-nitrobenzyl malonate as claimed in claim 1 or 2, is hydrolyzed to thereby give p-nitrobenzyl alcohol which is then used as the starting material.

5. A process for producing mono-p-nitrobenzyl malonate as set forth in claim 1 or 2 wherein di-p-nitrobenzyl malonate, which is contained in the reaction mixture after the extraction of mono-p-nitrobenzyl malonate in the process for producing mono-p-nitrobenzyl malonate as claimed in claim 1 or 2, is converted into mono-p-nitrobenzyl malonate by reacting with malonic acid.

\* \* \* \* \*